(12) United States Patent
Klare et al.

(10) Patent No.: US 10,623,874 B2
(45) Date of Patent: Apr. 14, 2020

(54) MILLING BLANK FOR THE PRODUCTION OF MEDICAL-TECHNICAL MOLDED PARTS

(71) Applicant: Pro3dure Medical GmbH, Dortmund (DE)

(72) Inventors: Martin Klare, Dortmund (DE); Frank Gischer, Menden (DE)

(73) Assignee: PRO3DURE MEDICAL GMBH, Dortmund (DE)

( * ) Notice: Subject to any disclaimer, the term of this patent is extended or adjusted under 35 U.S.C. 154(b) by 0 days.

(21) Appl. No.: 15/518,872

(22) PCT Filed: Oct. 13, 2015

(86) PCT No.: PCT/EP2015/073636
§ 371 (c)(1),
(2) Date: Apr. 13, 2017

(87) PCT Pub. No.: WO2016/059029
PCT Pub. Date: Apr. 21, 2016

(65) Prior Publication Data
US 2017/0230770 A1    Aug. 10, 2017

(30) Foreign Application Priority Data
Oct. 14, 2014  (DE) .................. 10 2014 114 895

(51) Int. Cl.
 H04R 25/00    (2006.01)
 A61C 13/00    (2006.01)
 A61K 6/00     (2020.01)
(52) U.S. Cl.
 CPC ....... H04R 25/652 (2013.01); A61C 13/0022 (2013.01); A61K 6/0047 (2013.01); H04R 25/658 (2013.01); A61K 6/00 (2013.01)
(58) Field of Classification Search
 CPC ............................ H04R 25/00; A61C 13/00
 USPC ...................................................... 524/81
 See application file for complete search history.

(56) References Cited

U.S. PATENT DOCUMENTS

| 4,115,346 A | 9/1978 | Gross et al. |
| 4,575,330 A | 3/1986 | Hull |
| 4,906,446 A | 3/1990 | Engelbrecht et al. |
| 5,487,012 A | 1/1996 | Topholm et al. |
| 5,663,214 A | 9/1997 | Okada |
| 5,707,611 A | 1/1998 | Ikemura et al. |
| 6,300,407 B1 * | 10/2001 | Machleder ........... C08K 5/0016 524/515 |
| 2002/0090525 A1 * | 7/2002 | Rusin ................. A61C 13/0022 428/542.8 |
| 2003/0153645 A1 * | 8/2003 | Sun ....................... A61K 6/0017 523/116 |
| 2008/0039646 A1 * | 2/2008 | Storzum ............... C07C 67/303 560/127 |
| 2013/0172441 A1 * | 7/2013 | Takahata ............ A61C 13/0022 523/115 |
| 2015/0165097 A1 * | 6/2015 | Parthasarathy ........ A61L 31/048 514/340 |
| 2017/0156990 A1 * | 6/2017 | Ruppert ............. A61C 13/0022 |

FOREIGN PATENT DOCUMENTS

| DE | 10011665 A1 | 9/2000 |
| DE | 19961341 A1 | 6/2001 |
| DE | 10147125 A1 | 4/2002 |
| DE | 102012022693 A1 | 5/2014 |
| EP | 0410034 A1 | 1/1991 |
| EP | 1702633 A2 | 9/2006 |
| WO | 01/87001 A2 | 11/2001 |

OTHER PUBLICATIONS

Otoplastik: Die individuelle Otoplastik zur Hörgeräteversorgung und als persönlicher Gehörschutz im Lärm, 4. überarbeitete Auflage (2013), S. 18 ff. von Voogdt ["Otoplastic: The individual otoplastic for hearing aid provision and as personal hearing protection in noisy environments", 4th revised edition (2013), p. 18 ff. by Voogdt].
A. Gärtner: "Weichmacher (DEHP) in Medizinprodukten" [Plasticizers (DEHP) in Medical Products]; mt-medizintechnik; Mar. 2007; TUEV Media Verlag Köln, pp. 92-102) (see p. 8).
International search report for application No. PCT/EP2015/073636 dated Feb. 5, 2016.
International Preliminary report on Patentability for Application No. PCT/EP2015/073636 dated Apr. 27, 2017.

* cited by examiner

*Primary Examiner* — Deve V Hall
(74) *Attorney, Agent, or Firm* — JMB Davis Ben-David

(57) ABSTRACT

A milling blank for producing medical-technical molded parts made from a material produced from at least two components, wherein a first component A comprises a poly(alkyl methacrylate) polymer, and wherein a second component B comprises at least one alkyl acrylate monomere and/or one alkyl methacrylate monomer, in which the poly(alkyl methacrylate) polymer of component A is at least partially soluble, wherein the material comprises a flexibilizer as a further component, wherein the flexibilizer is selected from the group of citric-acid-based, adipic-acid-based, phthalic-acid-based or aliphatic esters.

16 Claims, 1 Drawing Sheet

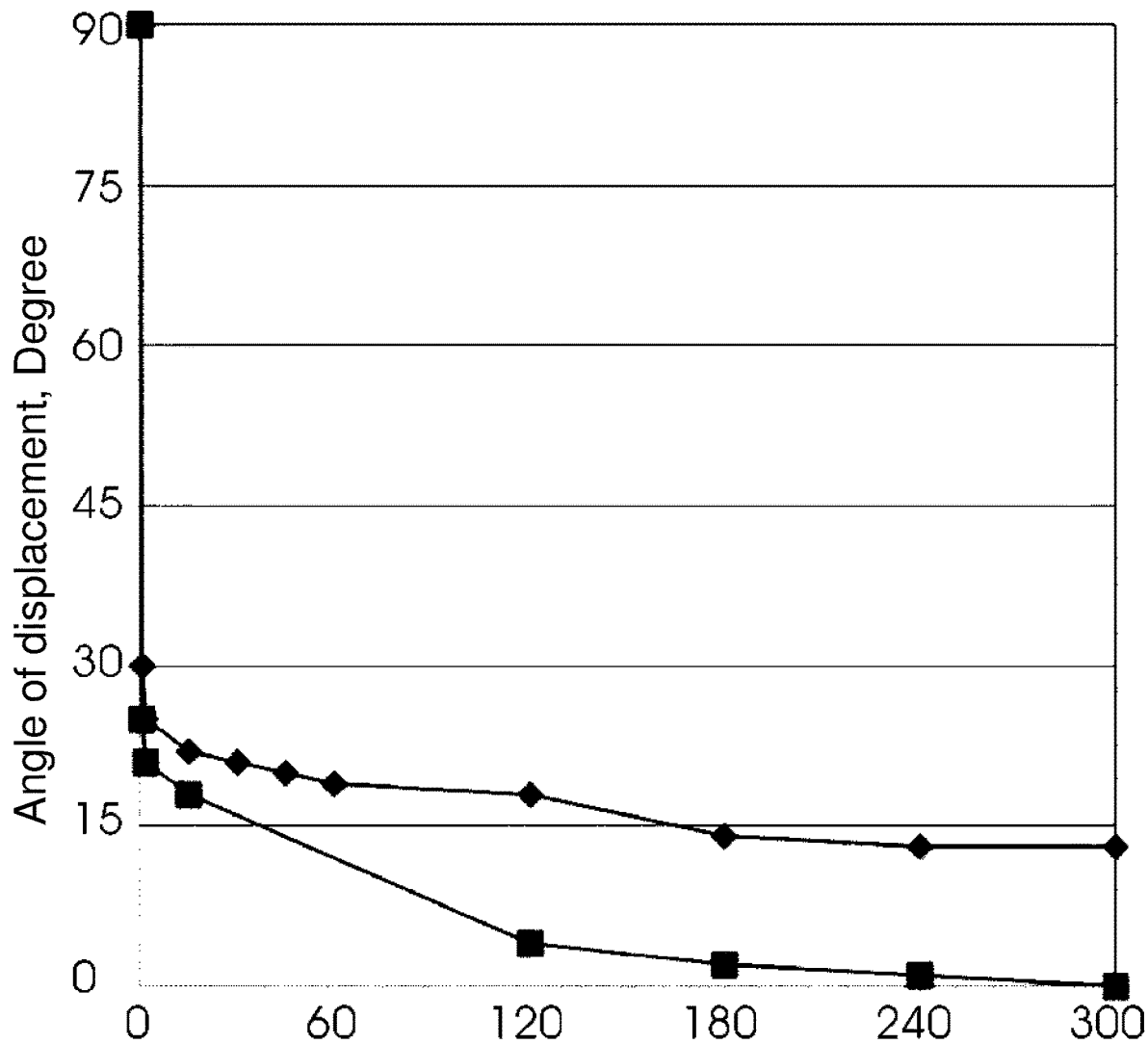

MILLING BLANK FOR THE PRODUCTION OF MEDICAL-TECHNICAL MOLDED PARTS

BACKGROUND OF THE INVENTION

The invention relates to a milling blank for the production of medical-technical molded parts, in particular dental splints or ear molds, as well as a method for the production of such a blank.

Blanks for the production of medical-technical molded parts of the initially named type are known in various designs from the prior art. Both dental splints as well as ear molds are currently produced substantially by means of two different methods of the prior art.

In the case of the first method known from the prior art, an impression of the positive (tooth crown or ear canal) is taken in a first step. Then, in the case of a dental splint, a positive plaster model is produced from the impression, on which then e.g. a splint (negative) is deep-drawn or a 2-component material is applied by means e.g. of a spreading technology and is then hardened. In the case of the so-called PNP process (positive-negative-positive) for the production of ear molds, the hearing aid acoustician takes in a first step an ear impression (positive) for the production of an otoplasty (for devices worn behind the ear) or a shell (for devices worn in the ear). In a second step, a negative mold (N) is prepared by means of the impression, into which either a radiation-curable or an autopolymerizing, low-viscosity formulation is subsequently poured. It is then hardened by means of heat in a pressure pot or by means of radiation.

The dental splint (negative) prepared in this manner or the ear mold (positive) must be optimally fitted for the anatomical conditions. Inaccurate molds would otherwise cause discomfort (e.g. pressure points, poor hold) and impair the function of the splint or hearing aid (e.g. misaligned teeth/feedback). As a result, it is important that the formulation has the lowest viscosity possible so that even undercuts and the finest surface textures are filled in with material and can be formed as true to detail as possible.

Additive layer processes such as e.g. stereolithography, are used as another method group of the prior art for the production of splints/ear molds, which functions based on digital data. It is thereby known from publication U.S. Pat. No. 4,575,330 that low-viscosity, radiation-curable resins or respectively resin mixes can be used for the production of three-dimensional objects by means of stereolithography. Furthermore, it is known from publications U.S. Pat. No. 5,487,012 and WO 01/87001 that the stereolithography can be used advantageously for the production of ear-pieces.

In the case of the stereolithographic method, three-dimensional objects made of a low-viscosity, radiation-curable formulation are structured in a manner that respectively one thin layer (approx. 25-100 μm) of the formulation is pre-cured by means of actinic radiation in a defined manner such that the created layer has the desired cross-sectional shape of the object at this position. The created layer is simultaneously polymerized on the layer cured in the previous step. The structure of the overall object can thus be accomplished with the help of a computer-controlled laser system such as e.g. an Nd:YVO$_4$ solid-state laser (Viper si$^2$ SLA System, 3D Systems, USA). The generated mold is postcured, if necessary, e.g. through radiation.

Special demands are made of the resin formulations that can be used in the stereolithographic process. In particular, the radiation sensitivity and the viscosity of the resin formulations as well as the strength of the molds precured by means of the laser curing should thereby be named. This not fully cured mold is called a green compact in stereolithographic technology and the strength of this green compact, characterized by the E module and the bending strength, is called green strength. The green strength is an important parameter in the practical application of stereolithography, since molds with a low green strength are deformed under their own weight during the stereolithography process or can sink or bend during the postcuring, for example with a xenon arc or halogen lamp.

Furthermore, for process-related reasons, the green compacts are built on supporting structures called supports. These supports must position the green compact in a stable manner during the entire production process since the position of the green compacts must not change due to the coating process. Accordingly, the supports for a stereolithographic process can only have a minimal flexibility.

For all of these reasons, it is only possible in a very limited manner to generate flexible ear molds on the basis of three-dimensional data. For one, it is necessary for the stereolithographic process to use the lowest-viscosity resins (<3 Pa s) possible. For this reason, certain material classes, such as silicone materials or highly filled composites, are not accessible or only accessible to a very limited degree.

This also applies to systems that have a so-called temperature-induced memory effect. However, this effect is useful for many medical-technical applications and is even essential for new applications. For example, a dental splint can be twisted during insertion in the mouth. Through the memory effect induced by the body heat, it is then molded back into the optimal position while it is worn. This considerably increases the wear comfort and prevents the generation of defective positions in comparison to a hard, deformed material.

SUMMARY OF THE INVENTION

Thus, the object of the invention is to provide a blank as well as a method for the production of a blank by means of which medical-technical molded parts, in particular dental splints or ear molds, can be produced in a simple and particularly precise manner, which parts furthermore have a temperature-induced memory effect.

The object is solved according to the invention by a blank as disclosed herein as well as a method. Advantageous further embodiments of the invention are also specified herein.

The milling blank according to the invention made of a material produced from at least two components for the production of medical-technical molded parts, in particular dental splints or ear molds, has as a first component A a poly(alkyl methacrylate) polymer, in particular a poly(alkyl methacrylate) polymer powder, and as a second component B at least one monomer, in which the poly(alkyl methacrylate) polymer of component A is at least partially, preferably completely, soluble, in particular an alkyl acrylate and/or an alkyl methacrylate monomer. Furthermore, the material contains a flexibilizer as a further component.

Due to the fact that biometric data for a plurality of medical-technical applications is increasingly available today and a digital workflow is not yet available for such materials, the invention allows to provide in an advantageous manner particularly easily machinable milling blanks for e.g. dental or respectively orthopedic jaw splints or ear molds, in particular based on three-dimensional data, in which the surface of the blanks is not smeared during the milling and the end product has a temperature-dependent memory effect. It is thus ensured that e.g. the ear mold can be inserted into the ear canal at room temperature in the hard elastic state and the deformation of the ear mold induced by the insertion (usually turning in) returns to the original state due to the body heat.

A milling blank is generally understood as a body made of a millable material, which can have any shape initially. The body is thereby preferably free of hollow spaces and/or is formed in a materially homogenous manner. Further preferably, the body has a smooth surface and/or a compact shape.

A material made of at least two components is a material that is formed by the mixture of the components, in particular through a chemical reaction of respectively at least one substance contained in the at least two components. Each of the at least two components can thereby be made of a single substance or can be made of a mixture of substances.

Component A is preferably substantially solid and/or component B is substantially liquid so that component A can be particularly easily dissolved in the liquid component B and can thereby be processed into a casting material.

The dissolving of one component in the other, in particular of component A in component B, is generally any process, in which the substance and/or particles of the one component are evenly distributed in the other component. In particular, in this context, the creation of a fine dispersion or respectively suspension can also be understood as dissolving.

The poly(alkyl methacrylate) polymer can generally be any polymer, the monomers of which comprise an alkyl methacrylate. This also generally includes all copolymers. However, the poly(alkyl methacrylate) polymer is preferably exclusively made of alkyl methacrylate monomers.

A polymer powder is a fine, granular mixture of the polymer, wherein the average grain size is preferably less than 1 mm, particularly preferably less than 500 μm and most preferably less than 100 μm.

A monomer is generally any chemical substance, which can be brought to polymerize with each other or under the addition of an additive. A monomer can generally also already be a dimer or a oligomer of a substance, which continues to be polymerization-capable.

The flexibilizer can first be any flexibilizer or respectively plasticizer known from the prior art.

According to an advantageous embodiment of the invention, component A comprises at least one poly(ethyl methacrylate) polymer (PEMA) or a poly(ethyl methacrylate) poly(methyl methacrylate) copolymer (PEMA-PMMA), in particular at least one PEMA powder or PEMA copolymer powder, whereby the milling blank can be produced in a particularly simple and particularly cost-effective manner and, moreover, has beneficial properties for medical-technical molded parts. Furthermore, other polymer powders such as PMMA poly(methyl methacrylate) in combination with the PEMA polymer powder can also be used.

According to a preferred further embodiment of the invention, component A consists up to at least 50%, preferably 60% and particularly preferably 70% with respect to the mass of component A of poly(ethyl methacrylate) polymer or copolymer.

According to a particularly preferred further embodiment of the invention, component A is made, except for a smaller share of additives, in particular of up to at least 90% and particularly preferably up to at least 95% with respect to the mass of component A of poly (ethyl methacrylate) polymer or poly (ethyl methacrylate) copolymer.

According to a preferred embodiment of the invention, the mass fraction of the polymer powder made of poly (ethyl methacrylate) polymer or poly (ethyl methacrylate) poly (methyl methacrylat) copolymer is at least 25%, preferably at least 45% and particularly preferably at least 50% of the total mass of the milling blank.

According to an advantageous further embodiment of the invention, component A comprises a catalyst, in particular an organic peroxide like benzoyl peroxide and/or toluidine, or barbituric acid or respectively a barbituric acid derivate, wherein the catalyst is preferably present in a concentration of 0.25-1 percent by weight. The admixing of a catalyst thereby improves in an advantageous manner the polymerization capability of the monomers contained in component B.

According to a further embodiment, a catalyst belonging to the group of barbituric acids and their derivates is preferred in the formulations according to the invention. In this case, the substances named in the following nonrestrictive list of barbituric acid derivates are particularly well applicable: barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-n-butylbarbituric acid, 1,3-dimethyl-5-isobutylbarbituric acid, 1,3-dimethyl-5-tertbutylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-5-ethylbarbituric acid, 1-benzyl-5-phenylbarbituric acid and thiobarbituric acids as well as their salts. These compounds and applications are described in the publications U.S. Pat. Nos. 5,707,611, 5,663,214, 4,906,446 and 4,115,346.

According to a further embodiment of the invention, the alkyl acrylate and/or alkyl methacrylate monomer of component B is at least one monomer of the group methyl methacrylate, ethyl methacrylate, ethyl acrylate, ethoxyethyl acrylate, tetrahydrofurfuryl methacrylate, tetrahydrofurfuryl acrylate, isobornyl acrylate and/or isobornyl methacrylate and preferably ethoxyethyl methacrylate. However, the list of alkyl acrylate and/or alkyl methacrylate monomers should be considered nonrestrictive. They can also be used in combination and/or formulated with other compounds from the group of the acrylates or methacrylates. This includes for example: bisphenol-A-ethoxylate(2)dimethacrylate, bisphenol-A-ethoxylate(4)dimethacrylate, bisphenol-A-propoxylate(2)dimethacrylate, bisphenol-A-propoxylate(4)dimethacrylate as well as dimethacrylates of the (n)-alkoxylized bisphenol F like bisphenol-F-ethoxylate(2)dimethacrylate and bisphenol-F-ethoxylate (4)dimethacrylate, bisphenol-F-propoxylate(2)dimethacrylate, bisphenol-F-propoxylate(4) dimethacrylate and mixtures of these. Monomeric or oligomeric dimethacrylates based on bisphenol A, in particular the bisphenol-A-ethoxylate(2)dimethacrylate and the bisphenol-A-ethoxylate(4)dimethacrylate, are preferably used. This list should also be considered nonrestrictive.

According to an advantageous further embodiment of the invention, component B comprises at least 5%, preferably at least 10%, particularly preferably at least 20% with respect to the mass of component B of the alkyl acrylate and/or alkyl methacrylate monomers, whereby a good and complete solubility of the polymer of component A is achieved in a particularly simple manner.

According to a preferred embodiment of the invention, component B comprises at least two different alkyl acrylate and/or alkyl methacrylate monomers, which preferably have a common mass fraction of at least 50%, particularly preferably 70% and most preferably 80% with respect to the mass of component B, whereby the properties of the milling blank can be set in a particularly simple manner and a particularly cost-effective production is possible.

According to a further embodiment of the invention, the mass fraction of the plasticizer or respectively flexibilizer is at least 5 percent by weight, preferably at least 10 percent by weight and particularly preferably at least 15 percent by weight. The thermoelastic range of the cured end product can be shifted into the range of the body temperature in a particularly simple manner by means of the flexibilizer. The mass fraction of the flexibilizer can generally refer both to the total mass of the material as well as to the mass of one of the two components A or B. However, the flexibilizer is particularly preferably added to component B or respectively contained in this component before it is mixed with component A. If the mass fraction then only refers to component B, the mass fraction of the flexibilizer with respect to the total mass of the material thus also lies below 5 percent by weight, depending on the mixture ratio of components A and B. A particularly simple production of the milling blank is enabled through the addition of the flexibilizer as an additional component. Most preferably, the material only contains component A as well as component B containing the flexibilizer.

According to an also preferred embodiment of the invention, the flexibilizer is selected from the group of phthalic acid esters like diethylhexylphthalate (DEHP), of the group of aliphatic esters, in particular of the group of the alkylsulfonic acid esters of the phenol, of the group of citric-acid-based flexibilizers like citric acid triethyl ester or particularly preferably 1,2-cyclohexane dicarboxylic acid diisononyl ester, or of the adipic-acid-based flexibilizers like diethylhexyladipate or diethyloctyladipate.

In terms of the invention and in light of the medical-technical range of application, flexibilizers from the group of aliphatic esters, like 1,2-cyclohexane dicarboxylic acid diisononyl ester, are preferred (also see A. Gärtner: "Weichmacher (DEHP) in Medizinprodukten" [Plasticizers (DEHP) in Medical Products]; mt-medizintechnik; March 2007; TUEV Media Verlag Köln, pgs. 92-102).

According to a preferred embodiment of the invention, the mass ratio of component A to component B is 0.5-2, preferably 0.65-1.5 and particularly preferably 0.75-1, whereby the desired material properties and a particularly cost-effective production can be achieved at the same time.

According to an advantageous further embodiment of the invention, the material has a temperature-dependent memory effect so that the material, in particular a finished dental splint or an ear mold, returns to its original shape after a deformation from heating, in particular to a temperature of 37° C.

Furthermore, the invention relates to a method for the production of a milling blank produced from a material for medical-technical molded parts, wherein first respectively one component A comprising a poly(alkyl methacrylate) polymer and one component B comprising at least one monomer, in which the poly(alkyl methacrylate) polymer of component A is at least partially, preferably completely, soluble, are produced, followed by the mixing of components A, B and a flexibilizer as well as the subsequent curing of the mixture.

The method according to the invention enables in a particularly simple manner the production of a milling blank, wherein neither particular technical knowledge in the field of polymer sciences nor complex, technical equipment are necessary.

The production of a component is generally understood as any form of provision of this component. This can thereby concern the mixing of several individual components, the preparation of one or more constituents of a component, for example through comminution, but also the mere weighing, measuring or respectively taking from an already prepared individual package of the necessary quantity of the respective component or respectively constituents of a component.

According to an advantageous further embodiment of the method, the curing takes place at a temperature between 30° C. and 70° C., preferably between 40° C. and 60° C. and particularly preferably between 45° C. and 55° C. and/or over a duration of 20-90 minutes, preferably 30-60 minutes and particularly preferably 45 minutes, whereby a ready-to-use milling blank can be obtained without great energy expenditure.

According to a further advantageous embodiment of the method, the curing takes place in a pressure pot at an internal pressure of at least 3 bar, preferably at least 5 bar, whereby a speedy and blister-free curing is ensured.

BRIEF DESCRIPTION OF THE DRAWINGS

An exemplary embodiment of the invention is explained in greater detail below. The FIGURE shows:

FIG. 1 Time-dependent relaxation of test bodies (5×5×80 mm) at 23° C. (◆) and at 37° C. (■)

For the production of a milling blank for the production of medical-technical molded parts, a material produced from two components A and B is used, the compositions of which are shown in the below table.

|  | Mass fraction, % |
|---|---|
| Component A | |
| Poly(ethyl methacrylate) | 99 |
| 1-benzyl-5-phenylbarbituric acid | 1 |
| Component B | |
| Ethoxyethyl methacrylate | 49.73 |
| Tetrahydrofurfuryl methacrylate | 33.2 |
| 1,2-cyclohexane dicarboxylic acid diisononyl ester | 16.5 |
| Dilauryl dimethyl ammonium chloride | 0.4 |
| 1% copper(II)-acetylacetonate solution in MMA | 0.17 |

The two components according to the invention are mixed in a ratio A:B=100:75 with a spatula in a beaker and then cured in a pressure pot (Polymax, by company Dreve) at 50° C. and 6 bar for 45 minutes blister-free in a duplicating silicone mold. A milling blank with a diameter of 98 mm and a thickness of 18 mm is thereby obtained.

Test bodies of the dimension 5×5×80 mm are then generated from this milling blank by means of a milling machine (Otofab 1, by company procedure). Alternatively, medical-technical molded parts are manufactured based on three-dimensional data.

The test bodies are then tempered at 23° C. and at 37° C. for 24 h and then bent in the middle by 90°. The relaxation of the angle is subsequently recorded depending on the time at the two aforementioned temperatures in order to document the temperature-dependent memory effect. The results are shown in FIG. 1. It is thereby shown that the formulation according to the invention has a temperature-dependent memory effect, by means of which mold bodies, which are deformed at room temperature, almost return to their original shape from body heat.

The invention claimed is:

1. A milling blank for producing medical-technical molded parts made from a material produced from at least two components, wherein a first component A comprises a poly(alkyl methacrylate) polymer, and wherein a second component B comprises at least one alkyl acrylate monomer and/or one alkyl methacrylate monomer, in which the poly(alkyl methacrylate) polymer of component A is at least partially soluble, wherein the material comprises a flexibilizer as a further component, wherein the flexibilizer is selected from the group consisting of citric-acid-based, adipic-acid-based, phthalic-acid-based, and aliphatic esters, and wherein the flexibilizer is present in a concentration of at least 5 percent by weight in relation to the mass of one of the components A or B.

2. The milling blank according to claim 1, wherein component A comprises a poly(ethyl methacrylate) polymer (PEMA) or a poly(ethyl methacrylate) poly(methyl methacrylate) copolymer (PEMA-PMMA).

3. The milling blank according to claim 1, wherein component A is made up of 50%, with respect to the mass of component A of poly(ethyl methacrylate) polymer or copolymer.

4. The milling blank according to claim 1, wherein a mass fraction of at least 25% of the polymer powder is made of poly(ethyl methacrylate) polymer or poly(ethyl methacrylate) poly(methyl methacrylate) copolymer.

5. The milling blank according to claim 1, wherein component A comprises a catalyst, wherein the catalyst is present in a concentration of 0.25-1 percent by weight.

6. The milling blank according to claim 1, wherein the alkyl acrylate and/or alkyl methacrylate monomer of component B is at least one monomer of the group methyl methacrylate, ethyl methacrylate, ethyl acrylate, ethoxyethyl acrylate, tetrahydrofurfuryl methacrylate, tetrahydrofurfuryl acrylate, isobornyl acrylate and/or isobornyl methacrylate.

7. The milling blank according to claim 1, wherein component B comprises at least 5% with respect to the mass of component B of the alkyl acrylate and/or alkyl methacrylate monomer.

8. The milling blank according to claim 1, wherein component B comprises at least two different alkyl acrylate and/or alkyl methacrylate monomers.

9. The milling blank according to claim 1, wherein the flexibilizer is 1,2-cyclohexane dicarboxylic acid diisononyl ester.

10. The milling blank according to claim 1, wherein the mass ratio of components A and B is 0.5-2.

11. The milling blank according to claim 1, wherein the material has a temperature-dependent memory effect, so that the material returns to its original shape after a deformation during heating.

12. The milling blank according to claim 5, wherein the catalyst is selected from the group consisting of an organic peroxide, barbituric acid, barbituric acid derivative and combinations thereof.

13. The milling blank according to claim 6, wherein the alkyl acrylate and/or alkyl methacrylate monomer is ethoxy ethyl methacrylate.

14. The milling blank according to claim 8, wherein the at least two different akyl acrylate and/or alkyl methacrylate monomers have a common percent by weight of at least 50% with respect to the mass of component B.

15. The milling blank according to claim 11, wherein heating comprises heating to a temperature of 37° C.

16. A milling blank for producing medical-technical molded parts, consisting essentially of:
    a first component A comprising a poly(alkyl methacrylate) polymer;
    a second component B comprising at least one alkyl acrylate monomer and/or one alkyl methacrylate monomer, in which the poly(alkyl methacrylate) polymer of component A is at least partially soluble; and
    a flexibilizer selected from the group consisting of citric-acid-based, adipic-acid-based, phthalic-acid-based, and aliphatic esters,
wherein the flexibilizer is present in a concentration of at least 5 percent by weight in relation to the mass of one of the components A or B.

* * * * *